United States Patent

Warnant et al.

[11] 4,190,658
[45] Feb. 26, 1980

[54] 14-IMINO-(15H)-EBURNAMINE COMPOUNDS, COMPOSITIONS, METHODS OF USE AND PROCESS OF SYNTHESIS

[75] Inventors: Julien Warnant, Neuilly-sur-Seine; André Farcilli, Rosny-sous-Bois; Italo Medici, Bondy, all of France

[73] Assignee: Roussel Uclaf, Paris, France

[21] Appl. No.: 925,103

[22] Filed: Jul. 17, 1978

[30] Foreign Application Priority Data

Jul. 25, 1977 [FR] France .................. 77 22747

[51] Int. Cl.² .................. A61K 31/475; C07D 471/22
[52] U.S. Cl. ..................... 424/256; 546/51
[58] Field of Search .................. 260/293.53, 293.56; 424/256, 262; 546/42, 51

[56] References Cited

FOREIGN PATENT DOCUMENTS 2538095  3/1976  Fed. Rep. of Germany .

OTHER PUBLICATIONS

Cartier, D. et al., Bull. Soc. Chim. de France, 1976, pp. 1961-1962.

Primary Examiner—Alton D. Rollins
Assistant Examiner—Lisa Jones
Attorney, Agent, or Firm—Hammond & Littell, Weissenberger and Muserlian

[57] ABSTRACT

Novel eburnamenine derivatives of the formula

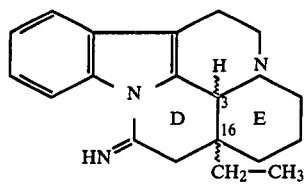

in the form of racemic mixtures or optically active isomers and their non-toxic, pharmaceutically acceptable acid addition salts which are oxygenators and cerebral vasoregulators of great value.

13 Claims, No Drawings

14-IMINO-(15H)-EBURNAMINE COMPOUNDS, COMPOSITIONS, METHODS OF USE AND PROCESS OF SYNTHESIS

STATE OF THE ART

French patent No. 2,342,065 and Chem. Abstr., Vol. 86 (1977), p. 190307b which is an abstract of Bull. Soc. Chim.de France, 1976, p. 1961–2 relate to different eburnamenine derivatives.

OBJECTS OF THE INVENTION

It is an object of the invention to provide the novel products of formula I and their non-toxic, pharmaceutically acceptable acid addition salts as well as novel processes for their preparation.

It is another object of the invention to provide novel pharmaceutical compositions and to a novel method of inducing increased oxygenation and cerebral vasoregulation in warm-blooded animals.

These and other objects and advantages of the invention will become obvious from the following detailed description.

THE INVENTION

The novel products of the invention are selected from the group consisting of racemic mixtures or optically active isomers of a member selected from the group consisting of compounds of the formula

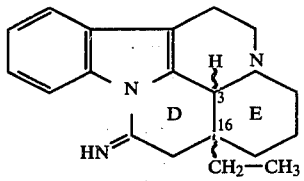

in the form of racemic mixtures or optically active isomers and their non-toxic, pharmaceutically acceptable acid addition salts. In the compounds of formula I, the 3-hydrogen and 16-ethyl group may have one or the other of α and β orientation which determines the existence of cis and trans diastereoisomers. In the products of formula I, the junction of the D and E rings may be cis or trans.

Examples of suitable acids for the non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, formic acid, benzoic acid, maleic acid, fumaric acid, succinic acid, tartaric acid, citric acid, oxalic acid, glyoxylic acid, aspartic acid and ascorbic acid, alkyl mono- and di-sulfonic acids such as methanesulfonic acid, ethanesulfonic acid, propanesulfonic acid, methanedisulfonic acid and α,β-ethanedisulfonic acid and aryl mono- and di-sulfonic acids such as benzenesulfonic acid.

Among the preferred compounds of the invention are the compounds of formula I wherein the 3-hydrogen and 16-ethyl group are in the cis position as well as their non-toxic, pharmaceutically acceptable acid addition salts that is to say in the said products the junction of the D and E rings is cis. The most preferred compound is (+) (3α,16α)-14-imino-(15 H)-eburnamenine.

The novel process of the invention for the preparation of a compound of formula I comprises reacting a compound of the formula

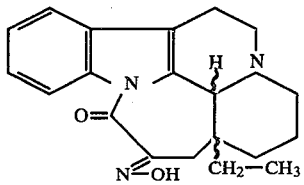

or an acid addition salt thereof with a basic agent to form the corresponding compound of formula I which, if desired, may be treated with an acid to form the corresponding acid addition salt. The reaction does not affect the structure of the molecule and therefore if the compound of formula II is cis (junction of D and E rings), the compound of formula I is cis. The racemic mixture of the compounds of formula I may be resolved by the known methods to obtain the optically active isomers.

In a preferred embodiment of the invention, (+) (3α,16α) 14,15-dihydro-15-hydroxyimino-D-homo-eburnamenin-14-one or one of its acid addition salts is treated with a base to form (+) (3α,16α) 14-imino-(15 H)-eburnamenine.

Examples of preferred conditions are the use of an acid addition salt of a compound of formula II such as the hydrochloride, phosphate or sulfate salts and preferably an excess of the base needed to neutralize the medium and to react with the compound of formula II is used. Examples of suitable bases are alkali metal or alkaline earth metal hydroxides such as sodium hydroxide, potassium hydroxide, lithium hydroxide and barium hydroxide.

The reaction is preferably effected hot with a preferred temperature of 100° to 150° C. The reaction is preferably effected in at least one organic solvent such as an alcohol, preferably an alcohol with a boiling point higher than 100° C. such as ethoxyethanol, ethylenegylcol, diethyleneglycol or triethyleneglycol or an aprotic solvent such as dimethylsulfoxide, with the organic solvent be used in admixture with water. The reaction is preferably effected at reflux of the mixture.

The said reaction may also be effected in water, preferably at 100° to 150° while operating under pressure. When using an aqueous medium, it is preferred to use a small volume of water to avoid a simultaneous hydrolysis of the product, more or less important according to the volume of the water used, which diminishes the yield of the reaction for the product of formula I. The undesired product of simultaneous hydrolysis of the compound of formula I has the formula

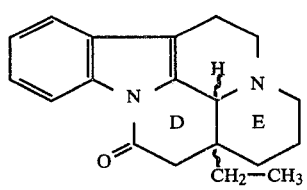

It is also an object of the invention to provide a process for the preparation of eburnamonines of formula III in the form of a racemic mixture or an optically active isomer by subjecting a compound of formula I or a non-toxic, pharmacetically acceptable acid addition salt thereof to the action of a hydrolysis agent. If the said addition salt of a compound of formula III is prepared, it may be reacted with a base to form the free base of formula III.

The transformation of the products of formula I into compounds of formula III does not affect the configuration of the molecule so that when the compound of formula I has a cis configuration at the junction of the D and E rings, the resulting configuration of the compound of formula III is also cis. Also, if the compound of formula I is an optically active isomer, so is the compound of formula III. A preferred embodiment of the invention comprises preparing (+) (3α,16α)-eburnamenin-14-(15 H)-one from (+) (3α,16α)-14-imino-(15 H)-eburnamenine.

In a preferred embodiment of the invention, the hydrolysis of the compound of formula I is most easily effected in an acid medium with an acid such as hydrochloric acid, sulfuric acid, phosphoric acid or formic acid, preferably at room temperature in water or in the presence of at least one organic solvent such as an alkanol like methanol or ethanol.

The hydrolysis of the compound of formula I may also be effected in a basic medium with a base such as an alkali metal hydroxide like sodium hydroxide, potassium hydroxide or lithium hydroxide. Equally useful are bases such as alkaline earth metal hydroxides like barium hydroxide or ammonium hydroxide and the hydrolysis is preferred effected at 100° to 150° C. under pressure.

In the process of the invention, it is also possible to prepare the compound of formula I and then to convert the same without isolation to the compound of formula III. For example, a compound of formula II may be reacted with a basic agent to form a compound of formula I which then can be subjected to acid hydrolysis to form the compound of formula III. Preferably, the compound of formula I is prepared in an aqueous medium and the hydrolysis is realized in proportion to its preparation. The compound of formula I may also be prepared in an aqueous medium and the hydrolysis may be effected in a basic medium.

The novel composition of the invention for oxygenation and cerebral vasoregulation are comprised of at least one compound selected from the group consisting of a compound of formula I and its non-tocic, pharmaceutically acceptable acid addition salts and a pharmaceutically acceptable carrier or excipient. The compositions may be in the form of tablets, dragees, gelules, granules, suppositories or injectable solutions or suspensions prepared in the usual manner.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, dispersants or emulsifiers.

The said compositions are useful in the treatment of cerebral vasculpathies and the syndromes provoked by an alteration of cerebral circulation; permit the prevention or diminishing of the effects of cerebral arteriosclerosis, of cerebral circulatory troubles, of meningia or cerebral hemorrages. They may also be used for the treatment of cerebral insufficiencies, cerebro-vascular accidents and of cranial traumatisms. Preferably, the compounds of formula I have the 3-hydrogen and the 16-ethyl group in the cis configuration and the preferred compounds is (+) (3α,16α)-14-imino-(15 H)-eburnamenine.

The novel method of the invention for increasing cerebral blood flow in warm-blooded animals, including humans, comprises administering to warm-blooded animals an amount of at least one compound of formula I and their non-toxic, pharmaceutically acceptable acid addition salts to increase the cerebral blood flow. The compounds may be administered orally, rectally or parenterally. The usual daily dose is 0,2 to 4 mg/kg depending on the specific compound and the method of administration.

The compounds of formula II may be prepared by the process described in French patents No. 2,081,593 and No. 2,104,959 and the salts thereof may be made in the usual manner.

In the following examples there are described several preferred embodiments to illustrate the invention. However, it is to be understood that the invention is not intended to be limited to the specific embodiments.

EXAMPLE 1

(+) (3α,16α)-14-imino-(15 H)-eburnamenine

STEP A: (+) (3α,16α)-14,15-dihydro-15-hydroxyimino-D-homo-eburnamenin-14-one hydrochloride 2 liters of acetone were added to a solution of 208.8 g of (+) (3α,16α)-14,15-dihydro-15-hydroxyimino-D-homo-eburnamenin-14-one in 500 ml of toluene and then 58 ml of 22° Bé hydrochloric acid (42.8 g of HCl per 100 ml=24.8 g of pure HCl) were added thereto at 20°–21° C. with stirring over 10 to 15 minutes under argon. Crystallization started at the beginning of the addition and at the end of the addition a yellow suspension was obtained. The mixture was stirred for one hour at 20° C. and was vacuum filtered. The recovered product was empasted twice with 150 ml of acetone each time and was then dried at 40° C. under reduced pressure in an oven for 16 hours to obtain 219.8 g (95% yield) of (+) (3α,16α)-14,15-dihydro-15-hydroxyimino-D-homo-eburnamenin-14-one with a specific rotation of $[\alpha]_D^{20} = 77° \pm 2°$ (c=1% in pyridine).

STEP B: (+) (3α,16α)-14-imino-(15 H)-eburnamenine

A mixture of 100 g of the product of Step A, 250 ml of ethoxyethanol and 32.1 g of sodium hydroxide pellets was stirred for one hour and was then heated at reflux which was maintained for 24 hours. The reaction mixture was cooled slightly and was then poured into 1200 g of ice. The mixture was stirred for one hour and was then vacuum filtered. The recovered product was washed with water and dried at 60° C. in an oven to obtain 69.2 g of raw product. 20 g of the said product were crystallized from 60 ml of methanol by treating the solution for 10 minutes with 0.4 g of activated carbon, filtering the solution and rinsing the filter twice with 5 ml of boiling methanol and cooling the filtrate at 0° to 5° C. for one hour. The mixture was vacuum filtered and the crystals were washed twice with 10 ml of iced methanol to obtain 12.2 g of (+) (3α,16α)-14-imino-(15 H)-eburnamenine melting at 161° C.and having a specific rotation of $[\alpha]_D^{20} = -92° \pm 1.5°$ (c=0.5% in CHCl$_3$).

Analysis: $C_{19}H_{23}N_3$

| Calculated: | % C | 77.77 | % H | 7.90 | % N | 14.32 |
|---|---|---|---|---|---|---|
| Found: | | 78.1 | | 7.9 | | 14.0 |

| U.V. Spectrum (ethanol): | | |
|---|---|---|
| max. at 242 nm | $E_1^1 = 647$ | $\epsilon = 18,900$ |
| max. at 274 nm | $E_1^1 = 349$ | $\epsilon = 10,200$ |
| max. at 292 nm | $E_1^1 = 256$ | $\epsilon = 7,500$ |
| max. at 302 nm | $E_1^1 = 245$ | $\epsilon = 7,200$ |

EXAMPLE 2

(+) (3α,16α)-eburnamenin-14-(15 H)-one

A mixture of 20 g of (+) (3α,16α)-14-imino-(15)-eburnamenine of Example 1, 100 ml of methanol, 20 ml of acetic acid and 10 ml of demineralized water was held at 21°-22° C. for 48 hours and was then poured into 1000 ml of cold water. 40 ml of concentrated ammonium hydroxide were added thereto and the mixture was stirred for 30 minutes and was then vacuum filtered. The recovered product was washed with water and was dried in an oven at 60° C. to obtain 19.85 g of raw product. 20 g of the raw product was dissolved in 50 ml of methylene chloride and the solution was filtered. The filter was rinsed with methylene chloride and the filtrate was distilled to dryness under reduced pressure. The residue was taken up in 20 ml of methanol at 20°-22° C. and the mixture was vacuum filtered. The recovered product was washed twice with 10 ml of methanol to obtain 19.1 g of pure (+) (3α,16α)-eburnamenin-14-(15)-one melting at 174.5° C. and having a specific rotation of $[\alpha]_D^{20} = -90° \pm 2°$ (c=1% in $CHCl_3$)

EXAMPLE 3

(+) (3α,16α)-eburnamenin-14-(15 H)-one

A suspension of 800 ml of ethoxyethanol, 64.2 g of sodium hydroxide pellets and 200 g of (+) (3α,16α)-14,15-dihydro-15-hydroxyimino-D-homo-eburnamenin-14-one hydrochloride was stirred for one hour and was then refluxed for 24 hours. The ethoxyethanol was distilled at 70° C. under a pressure of 10 mm Hg and the residue was taken up in 800 ml of water. 200 ml of hydrochloric acid were slowly added thereto and the solution was heated at 90°-95° C. for 30 minutes and was then poured into 1000 g of ice. The mixture was made alkaline by the slow addition of 250 ml of concentrated sodium hydroxide solution and was extracted once with 500 ml and four times with 200 ml of methylene chloride. The combined organic extracts were dried and evaporated to dryness. The residue was taken up in 100 ml of methanol which was then evaporated to dryness. The residue was taken up in 200 ml of methanol and the solution was refluxed for 15 minutes. After cooling to 20° C., the mixture was held at 20° C. for 30 minutes and was then vacuum filtered. The recovered product was washed three times with 50 ml of methanol and was dried at 60° C. to obtain 138.4 g of (+) (3α,16α)-eburnamenin-14-(15 H)-one melting at 175° C. and having a specific rotation of $[\alpha]_D^{20} = -92° \pm 2°$ (c=1% in $CHCl_3$) which was identical to the product of Example 2. Another 4.8 g of product was recovered from the crystallization mother liquors.

EXAMPLE 4

(+) (3α,16α)-eburnamenin-14-(15 H)-one

A mixture of 45 g of (+) (3α,16α)-14,15-dihydro-15-hydroxyimino-D-homo-eburnamenin-14-one, 246.7 ml of N sodium hydroxide solution and 1103 ml of demineralized water in an autoclave was stirred at room temperature for one hour and was heated to an interior temperature of 130°-135° C. The autoclave interior pressure was stabilized at 2.5±0.1 Kg and these conditions were maintained for 24 hours. The mixture was then cooled to 25° C. and was extracted three times with 150 ml of methylene chloride. The extracts were dried and evaporated to dryness and the residue was taken up in 45 ml of methanol. The mixture was evaporated to dryness and the residue was again taken up in 45 ml of methanol. The mixture was stirred at 20°-25° C. for 30 minutes and was then vacuum filtered. The product was rinsed 3 times with 15 ml of methanol to obtain 29.15 g of (+) (3α,16α)-eburnamenin-14-(15 H)-one melting at 175° C. and having a specific rotation of $[\alpha]_D^{20} = -93° \pm 2°$ (c=0.5% in $CHCl_3$) which was identical to the product of Example 2.

EXAMPLE 5

(+) (3α,16α)-eburnamenin-14-(15 H)-one

A mixture of 1.5 g of (+) (3α,16α)-14-imino-(15 H)-eburnamenine, 10.48 ml of N sodium hydroxide solution and 26.2 ml of demineralized water in an autoclave was heated on an oil bath to 150° C. for 24 hours with stirring. The interior temperature was 135° C. and the pressure was 2.5 kg and the apparatus was cooled to 20° C. The mixture was extracted with methylene chloride and the organic extracts were washed with water, dried, filtered and evaporated to dryness. The residue was taken up in 1.5 ml of methanol and the mixture was held at 18°-20° C. for one hour and was vacuum filtered. The product was rinsed and dried to obtain 1.31 g of (+) (3α,16α)-eburnamenin-14-(15 H)-one melting at 175° C. and having a specific rotation of $[\alpha]_D^{20} = -91.5° \pm 2°$ (c=1% in chloroform) which was identical to the product of Example 2.

EXAMPLE 6

Tablets were prepared containing 30 mg of (+) (3α,16α)-14-imino-(15 H)-eburnamenine and an excipient of lactose, treated starch, wheat starch, rice starch, talc and magnesium stearate. Gelules were prepared containing 30 mg of (+) (3α,16α)-14-imino-(15 H)-eburnamenine and sufficient excipient of talc, aerosil and magnesium stearate for a total weight of 150 mg.

PHARMACOLOGICAL DATA

A. Acute toxicity

The acute toxicity was determined on groups of 5 or 10 male mice weighing between 20–22 g which were fasted for 5 hours. The test products were orally administered in suspension in a solution of 0.5% of methylcellulose with an esophagus probe. The mortality was determined daily for one week and the lethal dose ($LD_{50}$) was determined to be greater than 1000 mg/kg for the product of Example 1.

B. Hypobaric oxygen

Groups of 10 male mice weighing 20–22 g and fasted for 5 hours received orally the test product in a solution of 0.5% of methylcellulose. 15 minutes after the administration, the animals were placed in a 2 liter dessiccator and the air was rapidly evaporated to a pressure of 90 mm Hg with a pump. The time of survival was expressed in seconds and the increase in survival time expressed in percent of treated animals to control animals under the same conditions was determined. The product of Example 1 at a dose of 100 mg/kg increased the survival time by 50%.

C. Vertebral and femoral flow in dogs

This study was effected with an open thorax on Beagle dogs of both sexes weighing 10 to 13 kg and anesthesized with chloralose. The vertebral flow was measured in ml/min with a Statham electromagnetic flow meter placed at the beginning of the right vertebral artery and the femoral flow was measured under the same conditions at the right femoral artery. By other means, the arterial pressure and the cardiac frequency were determined and the different parameters were determined before and after the injection of the compound of Example 1 and the maximum variations were calculated in percent. The results are reported in Table I wherein n is the number of tests for each dose of the product.

TABLE I

| PRODUCT | DOSES in mg/kg | Average arterial pressure | n | Cardiac Frequency | n | Vertebral flow | n | Femoral flow | n |
|---|---|---|---|---|---|---|---|---|---|
| | 0,1 | 4,7 ± 3,7 | 3 | −2,3 ± 2,3 | 3 | 26 ± 3,8 | 3 | 27,7 ± 8,9 | 3 |
| Example 1 | 0,3 | 2,3 ± 3,8 | 6 | −2 ± 4,4 | 6 | 28 ± 15,5 | 6 | 17,3 ± 18,2 | 6 |
| vincamine | 0,1 | −6,5 ± 6,5 | 2 | −10 ± 10 | 2 | 5 ± 5 | 2 | 17 | 1 |
| | 0,3 | −0,6 ± 1,4 | 5 | −15,2 ± 4,3 | 5 | 1,0 ± 11,5 | 5 | −2,8 ± 2,8 | 4 |

The results of the above test show that the product of Example 1 at a dose of 0.1 mg/kg administered intravenously increases vertebral flow without noticeably modifying arterial pressure or cardiac frequency as well as increasing femoral flow. Vincamine at the same doses modifies vertebral and femoral flow in an irregular fashion which is shown by the average mean-type values and provokes a slight diminution of cardiac frequency.

Various modifications of the products and process of the invention may be made without departing from the spirit or scope thereof and it is to be understood that the invention is intended to be limited only as defined in the appended claims.

We claim:

1. A compound selected from the group consisting of a compound of the formula

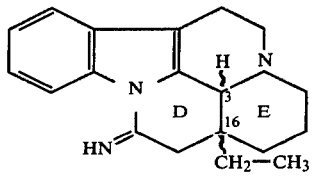

in the form of racemic mixtures or optically active isomers and their non-toxic, pharmaceutically acceptable acid addition salts.

2. A compound of claim 1 wherein the 3-hydrogen and 16-ethyl group are in the cis configuration.

3. A compound of claim 1 which is (+) (3α,16α)-14-imino-(15 H)-eburnamenine.

4. A process for the preparation of a compound of claim 1 consisting of the steps of reacting a compound of the formula

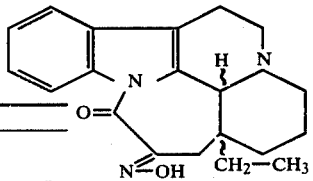

or an acid addition salt thereof with a basic agent to form the corresponding compound of claim 1 which, if desired, may be treated with an acid to form the corresponding acid addition salts.

5. The process of claim 4 wherein the starting material is selected from the group consisting of (+) (3α,16α)-14,15-dihydro-15-hydroxyimino-D-homo-eburnamenin-14-one or an acid addition salt thereof.

6. The process of claim 4 wherein the agent is an alkali metal hydroxide.

7. The process of claim 4 wherein the reaction is effected at 100° to 150° C.

8. A composition for increasing cerebral blood flow and oxygen content comprising an effective amount of at least one compound of claim 1 and a pharmaceutical carrier.

9. A composition of claim 8 wherein the 3-hydrogen and 16-ethyl group are in the cis configuration.

10. A composition of claim 8 wherein the compound is (+) (3α,16α)-14-imino-(15 H)-eburnamenine.

11. A method of increasing blood oxygen levels and cerebral blood flow in warm-blooded animals comprising administering to warm-blooded animals an amount of at least one compound of claim 1 sufficient to increase blood oxygen content and cerebral blood flow.

12. The method of claim 11 wherein the 3-hydrogen and 16-ethyl group are in the cis configuration.

13. The method of claim 11 wherein the compound is (+) (3α,16α)-14-imino-(15 H)-eburnamenine.

* * * * *